(12) United States Patent
Barker et al.

(10) Patent No.: US 11,591,669 B2
(45) Date of Patent: Feb. 28, 2023

(54) METAL RECOVERY PROCESS

(71) Applicant: MINT INNOVATION LIMITED, Auckland (NZ)

(72) Inventors: Will Barker, Auckland (NZ); Oliver Crush, Auckland (NZ)

(73) Assignee: MINT INNOVATION LIMITED, Auckland (NZ)

(*) Notice: Subject to any disclaimer, the term of this patent is extended or adjusted under 35 U.S.C. 154(b) by 968 days.

(21) Appl. No.: 16/344,398

(22) PCT Filed: Oct. 31, 2017

(86) PCT No.: PCT/NZ2017/050142
§ 371 (c)(1),
(2) Date: Apr. 24, 2019

(87) PCT Pub. No.: WO2018/080326
PCT Pub. Date: May 3, 2018

(65) Prior Publication Data
US 2020/0048732 A1 Feb. 13, 2020

(30) Foreign Application Priority Data
Oct. 31, 2016 (NZ) .................................. 725785

(51) Int. Cl.
| | | |
|---|---|---|
| C02F 1/00 | (2006.01) |
| C02F 1/38 | (2006.01) |
| C02F 3/34 | (2006.01) |
| C12N 1/20 | (2006.01) |
| C22B 3/18 | (2006.01) |

(Continued)

(52) U.S. Cl.
CPC .............. C22B 3/18 (2013.01); C02F 1/001 (2013.01); C02F 1/385 (2013.01); C02F 3/341 (2013.01); C12N 1/20 (2013.01); C22B 3/24 (2013.01); C02F 2001/007 (2013.01); C02F 2101/20 (2013.01)

(58) Field of Classification Search
CPC ... C22B 3/18; C22B 3/24; C02F 1/001; C02F 1/385; C02F 3/341; C02F 2001/007; C02F 2101/20; C02F 1/286; C12N 1/20; Y02P 10/20; B01J 2220/4868
USPC .......................... 435/41, 168; 210/601, 631
See application file for complete search history.

(56) References Cited

U.S. PATENT DOCUMENTS

| | | | |
|---|---|---|---|
| 4,293,333 A | 10/1981 | Drobot |
| 4,769,223 A | 9/1988 | Volesky et al. |

(Continued)

FOREIGN PATENT DOCUMENTS

| | | |
|---|---|---|
| CN | 102366716 | 3/2012 |
| CN | 104220611 A | 12/2014 |

(Continued)

OTHER PUBLICATIONS

Extended European Search Report in corresponding European Application No. 17863691.6 dated Mar. 19, 2020. 8 pages.

(Continued)

Primary Examiner — Fred Prince
(74) Attorney, Agent, or Firm — Leason Ellis LLP

(57) ABSTRACT

The invention relates to a process for recovering metals from aqueous solutions or solid feedstocks such as ores and waste. In particular, the invention relates to a method of recovering a target metals using a microorganism.

20 Claims, 1 Drawing Sheet

(51) Int. Cl.
    *C22B 3/24* (2006.01)
    *C02F 101/20* (2006.01)

(56) References Cited

U.S. PATENT DOCUMENTS

| | | | | |
|---|---|---|---|---|
| 4,992,179 A | * | 2/1991 | Brierley | .......... C02F 1/286 |
| | | | | 210/679 |
| 5,152,969 A | * | 10/1992 | Kleid | .......... C22B 11/08 |
| | | | | 75/744 |
| 5,462,720 A | | 10/1995 | Aragones | |
| 5,914,441 A | | 6/1999 | Hunter et al. | |
| 2004/0197249 A1 | | 10/2004 | Wan et al. | |
| 2008/0142422 A1 | * | 6/2008 | Cotoras Tadic | .......... C02F 9/00 |
| | | | | 210/511 |
| 2011/0308355 A1 | | 12/2011 | Kato et al. | |
| 2012/0024795 A1 | | 2/2012 | Tadic et al. | |
| 2014/0144292 A1 | | 5/2014 | Konishi et al. | |
| 2015/0329935 A1 | | 11/2015 | Terashi et al. | |

FOREIGN PATENT DOCUMENTS

| | | |
|---|---|---|
| CN | 104312955 A | 1/2015 |
| CN | 106086417 | 11/2016 |
| DE | 1446618 A1 | 6/1996 |
| EP | 0181497 A1 | 10/1985 |
| EP | 0 432 935 A1 | 6/1991 |
| EP | 2813585 A1 | 12/2014 |
| EP | 3162905 A1 | 5/2017 |
| IN | 201917016339 | 8/2016 |
| JP | 61-158796 A | 7/1986 |
| JP | 2004-180582 A | 7/2004 |
| SG | 11201903153 A | 5/2019 |
| WO | 96/00308 A2 | 1/1996 |
| WO | 2009130006 A1 | 10/2009 |
| WO | WO 2014/067024 A1 * | 5/2014 |
| WO | 2014/112637 A1 | 7/2014 |
| WO | 2016156409 A1 | 10/2016 |
| WO | 2018/080326 A1 | 5/2018 |
| WO | 2018/084723 A | 5/2018 |

OTHER PUBLICATIONS

International Search Report and Written Opinion in corresponding International Patent Application No. PCT/NZ2017/050142 dated Jan. 16, 2018. 9 pages.
International Search Report and Written Opinion for related International Application No. PCT/NZ2018/050144, dated Dec. 18, 2018.
Extended European Search Report for related European Application No. 17866561.8 dated Nov. 22, 2019.
Jones et al., "Gold in Minerals and the Composition of Native Gold", Geology Survey Circular 612, 1969.
NCBI Taxonomy Browser Aureobasidium (NCBI), 2020.
Bejor et al., "Low-cost Harvesting of Microalgae Biomass from Water", International Journal of Develeopment and Sustainability, vol. 2 No. 1, 2013, pp. 1-11.
International Search Report and Written Opinion for related International Application No. PCT/NZ2017/050144, dated Nov. 30, 2018.
Pant et al., 'Chemical and biological extraction of metals present in E waste: A hybrid technology', Waste Management, May 2012, vol. 32, No. 5, pp. 979-990 whole document, see in particular: abstract; Section 5 at pp. 984-986; Table 5; Fig 5.
Extended European Search Report for related European Application No. 18867926.0 dated Jul. 20, 2022.
Cui J et al: "Metallurgical recovery of metals from electronic waste: A review" & Neil J Creamer et al. Palladium and gold removal and recovery from precious metal solutions and electronic scrap leachates by Desulfovibrio desulfuricans, 2008.
Neil J Creamer et al: "Palladium and gold removal and recovery from precious metal solutions and electronic scrap leachates by Desulfovibrio desulfuricans", 2006.
Bhat Vi Raja et al: "Development of an Integrated Model to Recover Precious Metals from Electronic Scrap—A Novel Strategy for E-Waste Management", 2012.

* cited by examiner

METAL RECOVERY PROCESS

CROSS-REFERENCE TO RELATED PATENT APPLICATIONS

This application is a U.S. National Stage Application under 35 U.S.C. § 371 of International Patent Application No. PCT/NZ2017/050142, filed Oct. 31, 2017, which claims the benefit of priority under 35 U.S.C. Section 119(e) of New Zealand Patent Application number NZ 725785 filed Oct. 31, 2016, both of which are incorporated by reference in their entireties. The International Application was published on May 3, 2018, as International Publication No. WO 2018/080326 A1.

FIELD OF INVENTION

The invention relates to a process for recovering metals from aqueous solutions or solid feedstocks such as ores and waste. In particular, biometallurgical techniques are utilised during the process.

BACKGROUND

There is an abundance of materials containing trace metals throughout the world, including aqueous solutions and solid materials. However, due to the relative scarcity of the metal component relative to the non-metal matrix, recovering these metals in efficient, environmentally safe ways is extremely challenging. For example, the removal of toxic metal ions from aqueous liquid waste streams is a significant challenge for a wide range of industries.

Similarly, as ore grades for the mining and refining of virgin metals decrease, increased interest is being shown in obtaining metals from sources such as low-grade mining ores, smelter tailings and electronic waste. Recovering metals from these feedstocks, however, is often economically prohibitive. Factors that influence the viability of any recovery process include the metal concentration of a feedstock (and hence the amount of feedstock required for processing); the presence of refractory materials; and the volume of effluent generated. There is therefore a place for alternative solutions that aim to mitigate at least some of these problems, thereby improving the economics for the recovery of metals from low-grade or recalcitrant feedstocks.

Traditional techniques for refining metals include pyrometallurgy and hydrometallurgy. In pyrometallurgy, a feedstock is smelted at high temperature (typically in the presence of a suitable reductant and/or catalyst). This requires a non-trivial energy input (and associated emissions), and therefore there is a practical minimum metal concentration required in a feedstock. In hydrometallurgy, the feedstock is treated with a lixiviant solution that leaches the desired metal (specifically or otherwise) into an ionic or complexed soluble form. Subsequent steps are required to recover the target metal from solution (e.g. electrowinning). Depending on the temperature and pressure requirements for leaching, this approach may allow for lower grade feedstocks to be processed in comparison to pyrometallurgy. Consideration needs to be made for the possible use of corrosive (e.g. acidic) or toxic (e.g. cyanide) solutions; any consumption of solution components during feedstock treatment; and dealing suitably with waste effluent. Pyrometallurgy and hydrometallurgy techniques are not mutually exclusive, and may be used sequentially over multiple steps to refine specific metals.

Recovery of gold from gold containing ores is a typical example of a hydrometallurgical approach that has a number of issues. The amount of gold in gold bearing ores has been declining for over a hundred years as easier to recover resources with higher gold content have been depleted through extensive mining. As such, hydrometallurgical techniques have been used to recover traces of gold from large volumes of rock. Cyanide-based lixiviants have been successfully employed for many years, but suffer from toxicity issues and challenges with processing certain ore types.

Waste electronic equipment, such as printed circuit boards from computers, cell phones, notebooks and LCD displays also contain an appreciable amount of precious metals (including gold). While much endeavour has been applied to recovering gold from e-waste using pyrometallurgy and hydrometallurgy approaches, sustainable success has yet to be achieved.

Biometallurgy is a more recent approach that uses microorganisms to expose, leach, bind and/or recover metals from a feedstock under ambient conditions (Zhuang et al, *Current Opinion in Biotechnology* 33, pp 327-335 (2015)). Using microorganisms may lower the minimum required grade of a feedstock further, or better enable the economic processing of feedstocks that are refractory to pyrometallurgy and/or hydrometallurgy processes. A common tradeoff, however, is reaction time: biometallurgy often requires weeks to years to recover a metal from a feedstock (e.g. bio-oxidation of refractory copper ores using sulfur reducing bacteria).

It is an object of the present invention to provide a method of recovering metals using biometallurgical techniques that complement or replace traditional pyrometallurgy and hydrometallurgy approaches. It is hoped that this will lead to the capture of value from low-grade or waste streams of metal that are currently neglected, or to at least provide the public with a useful choice in this regard.

SUMMARY OF THE INVENTION

The present invention responds to a need in the art. The present invention provides methods for recovering metals from aqueous solutions containing metal ions, or solid feedstocks containing metals.

In a first aspect, the invention provides a method of recovering a target metal from a pregnant aqueous solution containing the target metal, the method comprising:
  (a) a biosorption step comprising contacting a microorganism with the pregnant aqueous solution such that at least a portion of the target metal biosorb to the microorganism, wherein the microorganism becomes metal laden and the pregnant aqueous solution becomes a barren solution;
  (b) a separating step comprising substantially separating the metal laden microorganism from the barren solution; and
  (c) a recovery step comprising recovery of the target metal from the metal laden microorganism.

Preferably the pregnant aqueous solution contains more than 1000 ppm, or more than 500 ppm, or more than 200 ppm, or more than 100 ppm, or more than 50 ppm, or more than 20 ppm, or more than 10 ppm, or more than 5 ppm, or more than 1 ppm of the target metal.

Preferably the pregnant aqueous solution contains between about 0.1 ppm to 1500 ppm, or between about 0.1 ppm to 1000 ppm, or between about 0.1 ppm to 500 ppm, or between about 0.1 ppm to 200 ppm, or between about 0.1 ppm to 100 ppm, or between about 0.1 ppm to 50 ppm, or between about 0.1 ppm to 20 ppm of the target metal.

Preferably the pregnant aqueous solution contains between about 0.5 ppm to 1500 ppm, or between about 0.5 ppm to 1000 ppm, or between about 0.5 ppm to 500 ppm, or between about 0.5 ppm to 200 ppm, or between about 0.5 ppm to 100 ppm, or between about 0.5 ppm to 50 ppm, or between about 0.5 ppm to 20 ppm of the target metal. Preferably the pregnant aqueous solution contains between about 1 ppm to 1500 ppm, or between about 1 ppm to 1000 ppm, or between about 1 ppm to 500 ppm, or between about 1 ppm to 200 ppm, or between about 1 ppm to 100 ppm, or between about 1 ppm to 50 ppm, or between about 1 ppm to 20 ppm of the target metal.

Preferably the barren solution contains less than 0.1 ppm, or less than 1 ppm, or less than 2 ppm, or less than 5 ppm, or less than 10 ppm, or less than 20 ppm, or less than 50 ppm, or less than 100 ppm of the target metal. Preferably the barren solution contains between about 0.001 and 100 ppm, or between about 0.001 and 50 ppm, or between about 0.001 and 50 ppm, or between about 0.01 and 50 ppm of the target metal.

Preferably the pregnant aqueous solution contains at least 10 times more target metal than the barren solution. Preferably the pregnant aqueous solution contains at least 20 times, or at least 40 times, or at least 45 times or at least 50 times more target metal than the barren solution.

Preferably the metal laden microorganism includes greater than 100 ppm, or greater than 200 ppm, or greater than 500 ppm or greater than 1000 ppm or greater than 30.00 ppm of the target metal.

Preferably the concentration factor of the target metal from the pregnant aqueous solution to the microorganism is greater than 5 or greater than 10, or greater than 20, or greater than 50, or greater than 100, or greater than 900.

Preferably, in the biosorption step the microorganism is in contact with the pregnant aqueous solution for between about 0.5 and 48 hours. Preferably between about 0.5 and 24 hours, or between about 0.5 and 12 hours, or between about 0.5 and 4 hours, or between about 1 and 3 hours.

In particular embodiments, the target metal is gold.

Preferably the biosorption step is carried out at ambient temperature, for example between about 15 and 30° C.

Preferably the microorganism is an algae or bacteria. Preferably the microorganism is a Gram-negative or Gram-positive bacteria. Preferably the microorganism is of the genus *Pseudomonas, Escherichia, Bacillus, Desulfovibrio, Plectonema, Cupriavidus, Clostridium* or *Delftia*.

Preferably the microorganism is selected from an environment where the target metal is found in a physiologically relevant amount.

Preferably where the target metal is gold the microorganism is selected from *Cupriavidus metallidurans, Delftia acidovorans, Pseudomonas aeruginosa, P. putida, Desulfovibrio desulfuricans, Bacillus subtilis,* or *Plectonema boryanum*.

Preferably where the target metal is gold the microorganism is selected from environments in which gold is found in physiologically relevant concentrations. Preferably the microorganism is selected from *Cupriavidus metallidurans* or *Delftia acidovorans*.

In certain embodiments, the separation step includes at least one of:
  gravity separation of the metal laden microorganism from the barren solution and removal of the barren solution, centrifugation and removal of the barren solution;
  filtration of the metal laden microorganism from the barren solution.

In certain embodiments, the separating step comprises gravity separation of the metal laden microorganism from the barren solution, wherein at least 50% of the barren solution is removed.

Preferably at least 60%, or at least 70%, or at least of 80%, or at least 90%, or at least 95% of the barren solution is removed.

In certain embodiments, the separating step comprises separating the metal laden microorganism by centrifugation, wherein during the centrifugation at least 50% of the barren solution is removed from the metal laden microorganism. Preferably at least 60%, or at least 70%, or at least of 80%, or at least 90%, or at least 95% of the barren solution is removed during centrifugation.

In certain embodiments, the separating step comprises separating the metal laden microorganism by filtration, wherein during the filtration at least 50% of the barren solution is removed from the metal laden microorganism. Preferably at least 60%, or at least 70%, or at least of 80%, or at least 90%, or at least 95% of the barren solution is removed during filtration.

In certain embodiments the separating step includes drying the microorganism.

In certain embodiments, the recovery step includes contacting the metal laden microorganism with a condition which triggers the microorganism to substantially desorb the target metal.

Preferably, the condition is a solution containing a compound that triggers desorption of the target metal. Preferably, the solution contains one or more of cysteine, or thiosulphate, or thiourea. Additionally or alternatively, the condition triggers desorption of the target metal (in metallic or ion form). By way of example, the conditions may be of pH less than 5, or pH less than 4, or pH less than 3, or pH less than 2. Alternatively the conditions may be between pH 1 and 5, or between pH 2 and 5, or between 2 and 4. By way of further example, the conditions may be pH greater than 8, or pH greater than 9, or pH greater than 10, or pH greater than 11, or pH greater than 12. Alternatively may be between pH 8 and 13, or between pH 9 and 13, or between 10 and 13. Additionally or alternatively, the conditions may be at an oxidation-reduction potential suitable for desorption of the target metal. Alternatively the recovery step includes burning or chemical dissolution of the metal laden microorganism to desorb the target metal.

In a particular embodiment, the pregnant solution includes at least one further metal, in addition to the target metal. Preferably the microorganism preferentially biosorbs the target metal over the further metal in the biosorption step and the further metal remains in the barren solution in the separating step. Preferably the microorganism preferentially biosorbs the target metal over the further metal in the biosorption step such that the mass ratio of target metal to further metal in the microorganism increases by a factor of at least 2 when compared to the mass ratio in the pregnant solution, Preferably the mass ratio increased by a factor of at least 3, or at least 5, or at least 8, or at least 10, or at least 20, or at least 50, or at least 100, or at least 200. Preferably the target metal is gold. Preferably the further metal is selected from one or more of copper and nickel.

In a second aspect, the invention provides a method of recovering a target metal, the method comprising:
  (a) a dissolution step comprising dissolving the target metal from a solid feedstock material with a lixiviant to form a pregnant aqueous solution containing target metal ions;

(b) a biosorption step comprising contacting a microorganism with the pregnant aqueous solution such that at least a portion of the target metal ions biosorb to the microorganism wherein the microorganism becomes metal laden, and the pregnant aqueous solution becomes a barren solution;

(c) a separating step comprising substantially separating the metal laden microorganism from the barren solution; and (d) a recovery step comprising recovery of the target metal from the metal laden microorganism.

Preferably the pregnant aqueous solution contains more than 1000 ppm, or more than 500 ppm, or more than 200 ppm, or more than 100 ppm, or more than 50 ppm, or more than 20 ppm, or more than 10 ppm, or more than 5 ppm, or more than 1 ppm of the target metal.

Preferably the pregnant aqueous solution contains between about 0.1 ppm to 1500 ppm, or between about 0.1 ppm to 1000 ppm, or between about 0.1 ppm to 500 ppm, or between about 0.1 ppm to 200 ppm, or between about 0.1 ppm to 100 ppm, or between about 0.1 ppm to 50 ppm, or between about 0.1 ppm to 20 ppm of the target metal. Preferably the pregnant aqueous solution contains between about 0.5 ppm to 1500 ppm, or between about 0.5 ppm to 1000 ppm, or between about 0.5 ppm to 500 ppm, or between about 0.5 ppm to 200 ppm, or between about 0.5 ppm to 100 ppm, or between about 0.5 ppm to 50 ppm, or between about 0.5 ppm to 20 ppm of the target metal. Preferably the pregnant aqueous solution contains between about 1 ppm to 1500 ppm, or between about 1 ppm to 1000 ppm, or between about 1 ppm to 500 ppm, or between about 1 ppm to 200 ppm, or between about 1 ppm to 100 ppm, or between about 1 ppm to 50 ppm, or between about 1 ppm to 20 ppm of the target metal.

Preferably the barren solution contains less than 0.1 ppm, or less than 1 ppm, or less than 2 ppm, or less than 5 ppm, or less than 10 ppm, or less than 20 ppm, or less than 50 ppm, or less than 100 ppm of the target metal. Preferably the barren solution contains between about 0.001 and 100 ppm, or between about 0.001 and 50 ppm, or between about 0.001 and 50 ppm, or between about 0.01 and 50 ppm of the target metal.

Preferably the pregnant aqueous solution contains at least 10 times more target metal than the barren solution. Preferably the pregnant aqueous solution contains at least 20 times, or at least 40 times, or at least 45 times or at least 50 times more target metal than the barren solution.

Preferably the metal laden microorganism includes greater than 100 ppm, or greater than 200 ppm, or greater than 500 ppm or greater than 1000 ppm or greater than 30,000 ppm of the target metal.

Preferably the concentration factor of the target metal from the pregnant aqueous solution to the microorganism is greater than 5 or greater than 10, or greater than 20, or greater than 50, or greater than 100, or greater than 900.

Preferably, in the biosorption step the microorganism is in contact with the pregnant aqueous solution for between about 0.5 and 48 hours. Preferably between about 0.5 and 24 hours, or between about 0.5 and 12 hours, or between about 0.5 and 4 hours, or between about 1 and 3 hours.

In particular embodiments, the target metal is gold.

In certain embodiments the solid feedstock material comprises a solid material comprising less than 5%, or less than 1%, or less than 0.1%, or less than 0.01%, or less than 0.001%, or less than 0.0001% of target metal. In certain embodiments, the solid feedstock material is any one or more of an ore, a tailing or waste from an industrial process such as mining, a sand, a clay, a waste material such as e-waste.

In certain embodiments, the dissolution step and biosorption step may occur in the same vessel.

In certain embodiments where the target metal is gold, preferably the solid feedstock material is e-waste, or gold bearing ore, or gold bearing sand, or gold bearing clay.

In a particular embodiment, the pregnant solution includes at least one further metal, in addition to the target metal. Preferably the microorganism preferentially biosorbs the target metal over the further metal in the biosorption step and the further metal remains in the barren solution in the separating step. Preferably the microorganism preferentially biosorbs the target metal over the further metal in the biosorption step such that the mass ratio of target metal to further metal in the microorganism increases by a factor of at least 2 when compared to the mass ratio in the pregnant solution, Preferably the mass ratio increased by a factor of at least 3, or at least 5, or at least 8, or at least 10, or at least 20, or at least 50, or at least 100, or at least 200. Preferably the target metal is gold. Preferably the further metal is selected from one or more of copper and nickel.

In certain embodiments the lixiviant solution is a thiourea-based solution, or a thiosulphate-based solution, or a thiocyanate-based solution, or a cyanide-based solution, or a halogen-based solution, or an aqua regia-based solution.

In certain embodiments, the separation step includes at least one of:
gravity separation of the metal laden microorganism from the barren solution and removal of the barren solution, centrifugation and removal of the barren solution;
filtration of the metal laden microorganism from the barren solution.

In certain embodiments, the separating step comprises gravity separation of the metal laden microorganism from the barren solution, wherein at least 50% of the barren solution is removed.

Preferably at least 60%, or at least 70%, or at least of 80%, or at least 90%, or at least 95% of the barren solution is removed.

In certain embodiments, the separating step comprises separating the metal laden microorganism by centrifugation, wherein during the centrifugation at least 50% of the barren solution is removed from the metal laden microorganism. Preferably at least 60%, or at least 70%, or at least of 80%, or at least 90%, or at least 95% of the barren solution is removed during centrifugation.

In another embodiment, the separating step comprises separating the metal laden microorganism by filtration, wherein during the filtration at least 50% of the barren solution is removed from the metal laden microorganism. Preferably at least 60%, or at least 70%, or at least of 80%, or at least 90%, or at least 95% of the barren solution is removed during filtration.

In certain embodiments the separating step includes drying the microorganism.

An additional separation step may be required to separate the metal laden microorganism from the barren solution and remaining solid feedstock material.

In certain embodiments, the recovery step includes contacting the metal laden microorganism with a condition which triggers the microorganism to substantially desorb the target metal.

Preferably, the condition is a solution containing a compound that triggers desorption of the target metal. Preferably, the solution contains one or more of cysteine, or thiosulphate, or thiourea. Additionally or alternatively, the condition that triggers desorption of the target metal (in metallic or ion form). By way of example, the conditions may be of pH less than 5, or pH less than 4, or pH less than 3, or pH less than 2. Alternatively the conditions may be between pH 1 and 5, or between pH 2 and 5, or between 2 and 4. By way of further example, the conditions may be pH greater than 8, or pH greater than 9, or pH greater than 10, or pH greater than 11, or pH greater than 12. Alternatively may be between pH 8 and 13, or between pH 9 and 13, or between 10 and 13. Additionally or alternatively, the conditions may be at an oxidation-reduction potential suitable for desorption of target metal.

Alternatively the recovery step includes burning or chemical dissolution of the metal laden microorganism to desorb target metal.

In a third aspect, there is provided a target metal recovered by the methods of the first and/or second aspects. Preferably the metal is gold.

In a fourth aspect, there is provided a system for the recovery of a target metal from a pregnant aqueous solution containing the target metal, the system comprising:
(a) a vessel configured for contacting a microorganism with the pregnant aqueous solution such that at least a portion of the target metal biosorbs to the microorganism, wherein the microorganism becomes metal laden, and the pregnant aqueous solution becomes a barren solution;
(b) a separator configured for substantially separating the metal laden microorganism from the barren solution; and
(c) a recovery means configured for recovery of the target metal from the metal laden microorganism.

In certain embodiments, the system includes means for passing the barren solution containing metal laden microorganism from the vessel in (a) to the separator in (b). In certain embodiments, the system includes means for passing the metal laden microorganism in (b) to the recovery means in (c).

In certain embodiments, the separator comprises at least one of:
means for gravity separating of the metal laden microorganism from the barren solution wherein at least a portion of the barren solution is removed from the metal laden microorganism,
means for separating the metal laden microorganisms by centrifugation, wherein at least a portion of the barren solution is removed from the metal laden microorganism;
means for separating the metal laden microorganisms by filtration, wherein at least a portion of the barren solution is removed from the metal laden microorganism.

In certain embodiments, the separator comprises means for gravity separating the metal laden microorganism from the barren aqueous and removing at least a portion of the barren solution.

In certain embodiments, the separator comprises means for separating the metal laden microorganism by centrifugation, wherein at least a portion of the barren solution is removed from the metal laden microorganism.

In certain embodiments, the separator comprises means for separating the metal laden microorganism by filtration, wherein at least a portion of the barren solution is removed from the metal laden microorganism.

In certain embodiments, the recovery means includes an element for contacting the metal laden microorganism with a solution.

In certain embodiments, the recovery means includes an element for burning the metal laden microorganism to release the target metal.

In a fifth aspect, there is provided a system for the recovery of a target metal from a solid feedstock material, the system comprising:
(a) a vessel configured for dissolving target metal from a solid feedstock material with a lixiviant to form a pregnant aqueous solution containing the target metal;
(b) a vessel configured for contacting a microorganism with the pregnant aqueous solution such that at least a portion of the target metal biosorb to the microorganism, wherein the microorganism becomes metal laden, and the pregnant aqueous solution becomes a barren solution;
(c) a separator configured for substantially separating the metal laden microorganism from the barren solution; and
(d) a recovery means configured for recovery of the target metal from the metal laden microorganism.

In certain embodiments, the system includes means for passing the pregnant aqueous solution from the vessel in (a) to the vessel in (b). In certain embodiments, the vessel used in (a) may be the same as that used in (b). In certain embodiments, the system includes means for passing the barren solution containing metal laden microorganism from the vessel in (b) to the separator in (c). In certain embodiments, the system includes means for passing the metal laden microorganism in (c) to the recovery means in (d).

In certain embodiments, the separator comprises means for gravity separating the metal laden microorganism from the barren solution and decanting at least a portion of the barren solution.

In certain embodiments, the separator comprises at least one of:
means for gravity separating of the metal laden microorganism from the barren solution wherein at least a portion of the barren solution is removed from the metal laden microorganism,
means for separating the metal laden microorganisms by centrifugation, wherein at least a portion of the barren aqueous solution is removed from the metal laden microorganism;
means for separating the metal laden microorganisms by filtration, wherein at least a portion of the barren solution is removed from the metal laden microorganism.

In certain embodiments, the recovery means includes means for contacting the metal laden microorganism with a solution.

In certain embodiments, the recovery means includes means for burning the metal laden microorganism to release the target metal.

Preferably the microorganism is an algae or bacteria. Preferably the microorganism is a Gram-negative or Gram-positive bacteria. Preferably the microorganism is of the genus *Pseudomonas, Escherichia, Bacillus, Desulfovibrio, Plectonema, Cupriavidus, Clostridium* or *Delftia*.

Preferably the microorganism is selected from an environment where the target metal is found in a physiologically relevant amount.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures, in which.

DETAILED DESCRIPTION

Definitions

Figure 1:
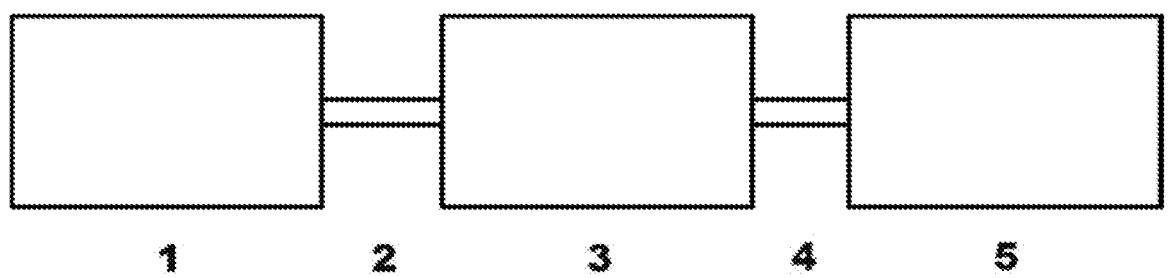
FIG. 1 represents a system configured for recovering target metal from a pregnant aqueous solution in accordance with the fourth aspect of the invention.

The term "target metal" includes both elemental metal and ions of a particular target metal or a plurality of particular metals. It is recognised that a particular target metal may exist in different ionic states (including elemental form) or a plurality of ionic states in different parts of the methods or systems of the invention. The target metal may be dissolved or partially dissolved in the aqueous solutions of the invention, either as an ion (or ions), salts or complex or elemental form or a combination thereof. Similarly, the target metal may exist in solid form either as an ion (or ions), salts or complex or elemental form or a combination thereof as the context dictates.

The term "pregnant aqueous solution" refers to an aqueous solution containing dissolved target metal. In some extreme instances a pregnant aqueous solution may also contain at least some undissolved target metal The term "barren solution" refers to an aqueous solution containing a depleted amount of dissolved target metal compared with the pregnant aqueous solution. It is recognised that in extreme cases the target metal may be completely absent in the barren solution.

The term "contacting" refers to the mixing and interaction between two or more solutions or substances. One example of this is the contact between a pregnant aqueous solution and a microorganism. A further example of this is the contact between a lixiviant and a solid feedstock material.

The terms "biosorb" and "biosorbent" and "biosorption" and the like, when used in relation to the methods and systems of the invention, refers to the microorganism(s) being used to adsorb, adsorp or absorb metal, or the process of metal adsorbing, adsorping or absorbing to the microorganism(s).

The term "feedstock" refers to the input material being processed.

The term "solid feedstock material" refers to the solid-state nature of various metal sources that may be the input for processing. Examples include mining ore, tailings and electronic waste.

The term "microorganism" refers to algae or bacteria or fungi or protoctist or archaea. It may be used in the plural sense for a mixture of microorganisms.

The term "metal laden microorganism" means a microorganism that has biosorbed one or more target metal.

The term "ppm" refers to parts per million and relates to the concentration of a substrate in comparison to another substrate. It refers to the weight:weight ratio between the two substrates. For an aqueous solution ppm and mg/L are approximately equivalent.

The term "rcf" means relative centrifugal force.

The term "decanted" or "decant" or the like refers to the removal of the upper portion of aqueous solution from a solid/aqueous mixture in which the solid fraction has been allowed to settle.

The term "lixiviant" refers to an aqueous solution that is capable of dissolving a target metal into an aqueous form.

The term "e-waste" refers to electronic waste or waste electrical and electronic equipment (commonly referred to as WEEE).

A "system" comprises pipework and other features that would be typically employed to enable the extraction of metals from a feedstock. By way of example, the "system" may include vessels, conduits, pumps, pressure valves, heat exchangers, filters, instrumentation (pressure sensors, flow sensors, pH sensors) and mixing tees (static mixers).

Discussion

While the following description focuses on particular embodiments of the invention, namely the recovery of gold from pregnant aqueous solutions or solid feedstock material, it should be appreciated that the invention may be applicable to production of alternative target metals as will be known by persons of ordinary skill in the art to which the invention relates.

As discussed hereinbefore, the inventors have devised methods for recovering metals from aqueous solutions containing metal ions and/or solid feedstock materials. In particular, the present invention provides methods for recovering metals from aqueous solutions in a manner that has a number of cost and environmental advantages over existing methods.

In a particular aspect of the invention there is provided a method of recovering a target metal from a pregnant aqueous solution containing the target metal, the method comprising:
(a) a biosorption step comprising contacting a microorganism with the pregnant aqueous solution such that at least a portion of the target metal biosorbs to the microorganism, wherein the microorganism becomes metal laden, and the pregnant aqueous solution becomes a barren solution;
(b) a separating step comprising substantially separating the metal laden microorganism from the barren solution; and
(c) a recovery step comprising recovery of the target metal from the metal laden microorganism.

FIG. 1 shows an embodiment of the invention in which a microorganism is contacted with a pregnant aqueous solution containing target metal ions in biosorption vessel 1. The invention has particular utility for concentrating dilute streams of target metal ions, so in some embodiments the pregnant aqueous solution contains more than 1000 ppm, or more than 500 ppm, or more than 200 ppm, or more than 100 ppm, or more than 50 ppm, or more than 20 ppm, or more than 10 ppm, or more than 5 ppm, or more than 1 ppm of the target metal. Preferably the pregnant aqueous solution contains between about 0.1 ppm to 1500 ppm, or between about 0.1 ppm to 1000 ppm, or between about 0.1 ppm to 500 ppm, or between about 0.1 ppm to 200 ppm, or between about 0.1 ppm to 100 ppm, or between about 0.1 ppm to 50 ppm, or between about 0.1 ppm to 20 ppm of the target metal.

Preferably the pregnant aqueous solution contains between about 0.5 ppm to 1500 ppm, or between about 0.5 ppm to 1000 ppm, or between about 0.5 ppm to 500 ppm, or between about 0.5 ppm to 200 ppm, or between about 0.5 ppm to 100 ppm, or between about 0.5 ppm to 50 ppm, or between about 0.5 ppm to 20 ppm of the target metal. Preferably the pregnant aqueous solution contains between about 1 ppm to 1500 ppm, or between about 1 ppm to 1000 ppm, or between about 1 ppm to 500 ppm, or between about 1 ppm to 200 ppm, or between about 1 ppm to 100 ppm, or between about 1 ppm to 50 ppm, or between about 1 ppm to 20 ppm of the target metal.

In accordance with the methods of the invention, in certain embodiments lixiviant solutions containing target metal ions serve as a pregnant aqueous solution. By way of non-limiting example, when gold is the target metal, the pregnant aqueous solution may be produced by dissolving the target metal in a thiourea-based solution, or a thiosulphate-based solution, or a thiocyanate-based solution, or a cyanide-based solution, or a halogen-based solution, or an aqua regia-based solution, and examples of suitable conditions can be found in Aylmore, *Developments in Mineral Processing* 15, pp 501-539 (2005).

Upon contact with the pregnant solution the microorganism biosorbs the target metal over a time period necessary to biosorb at least 50% of the target metal. In particular embodiments, the microorganism is contacted with the pregnant aqueous such that at least 60%, or at least 70%, or at least 80%, or at least 90%, or at least 95% of the target metal is biosorbed. The time period is preferably, between about 0.5 and 48 hours, or between about 0.5 and 24 hours, or between about 0.5 and 12 hours, or between about 0.5 and 4 hours, or between about 1 and 3 hours.

In a particular preferred embodiment of the invention, the microorganism preferentially biosorbs the target metal over a further metal or metals in the pregnant solution. The further metal(s) is then separated from the target metal in the separation step while the further metal remains in the barren solution. Examples 7 and 8 show the preferential nature of the biosorption step. The factor of preferential biosorption will in part depend on the ratio of the metals in the pregnant solution, for example if they are already in similar quantities the mass ratio may not change as much as if there is a large excess of the further metal. However, preferably the microorganism preferentially biosorbs the target metal over the further metal in the biosorption step such that the mass ratio of target metal to further metal in the pregnant solution compared to the ratio of the target metal of the further metal biosorbed to the microorganism increases by a factor of at least 2, or at least 3, or at least 5, or at least 8, or at least 10, or at least 20, or at least 50, or at least 100, or at least 200. The upper limit of the increase in ratio will in part be dependent on the starting ratio, but may be 1,000 or higher. Preferably the target metal is gold. Preferably the further metal is selected from one or more of copper and nickel.

A number of microorganisms are capable of biosorbing metal ions. The microorganism is preferably an algae or bacteria, preferably a Gram-negative or Gram-positive bacteria, for example from of the genus *Pseudomonas*, *Escherichia*, *Bacillus*, *Desulfovibrio*, *Plectonema*, *Cupriavidus*, *Clostridium* or *Delftia*. The microorganism is preferably selected from an environment where the target metal is found in a physiologically relevant amount, for example lower than 0.5 ppm. Examples of microorganisms are capable of biosorbing metal ions include the Gram-negative bacteria *Pseudomonas aeruginosa* and *Escherichia coli*, the Gram-positive bacterium *Bacillus subtilis*, and the fungi *Saccharomyces cerevisiae*. Nancharaiah et al (*Trends in Biotechnology* 34, pp 137-155 (2016)), incorporated herein by reference, identifies the wide range of microorganisms that may be employed to biosorb target metals in accordance with the methods of the invention. The majority of biosorption events are adsorptive in nature (i.e. metal ions are bound to the surface of a microorganism through passive interaction with cell wall or membrane moieties), but some are absorptive (i.e. metal ions are actively internalised by a microorganism).

In particular embodiments wherein the target metal ion is gold, microorganisms such as the Gram-negative bacteria *Pseudomonas aeruginosa, P. putida* and *Desulfovibrio desulfuricans*, Gram-positive bacteria *Bacillus subtilis*, and/or the algae *Plectonema boryanum* have been shown to biosorb gold (Reith et al, *International Society for Microbial Ecology Journal* 1, pp 567-584 (2007)). In certain preferred embodiments, the microorganism is selected from environments in which gold is found in physiologically relevant concentrations, such as the Gram-negative bacteria *Cupriavidus metallidurans* and *Delftia acidovorans* (Rea et al, *FEMS Microbiology Ecology* 92, pp fiw082 (2016)). In other preferred embodiments, the microorganism is selected from those used in other industrial processes, such as the Gram-positive bacterium *Clostridium autoethanogenum* (Abrini et al, *Arch Microbiol* 161, pp 345-351 (1994)).

When used in the invention, rather than in the environment, the microorganism is generally a monoculture, or at least a limited mixture of two to five microorganisms. Further, in the natural environment, the microorganism is generally only exposed to low levels of the target metal, for example, less than 0.5 ppm. In preferred embodiments of the invention, the pregnant solution contains relatively high amounts of target metal, for example greater than 0.5 ppm or greater than 1 ppm. It is therefore surprising the microorganism still has the capacity to biosorb higher levels of target metal. Additionally or alternatively, it is surprising that the microorganism is able to biosorb the target metal in relatively short time periods, for example less than 12 hours, even where the target metal is at low or higher concentrations.

The inventors have found *Cupriavidus metallidurans* (*C. metallidurans*) to be particularly useful in the present invention where gold is the target metal. The inventors have found *C. metallidurans* to be relatively easy to grow, good at biosorbing gold and/or biosorbs the target metal relatively quickly and/or is good for preferentially biosorbing gold (see Example 7 and 8) and/or is relatively tolerant to other metals being present in the pregnant solution.

In particular embodiments wherein the target metal ion is gold, and the pregnant aqueous solution is a thiosulphate-based solution, or a cyanide-based solution, or a chloride-based solution, *C. metallidurans* may be used to biosorb the gold-thiosulphate complex, or aurocyanide, or chloroaurate respectively (Reith et al, *PNAS* 106, pp 17757-17762 (2009); Etschmann et al, *Chemical Geology* 438, pp 103-111 (2016)).

Upon at least partial biosorption of the target metal ion, the solution becomes a barren solution, wherein the barren solution contains less of the target metal than the pregnant solution. In particular embodiments, the barren solution contains less than 0.1 ppm or less than 1 ppm, or less than 2 ppm, or less than 5 ppm, or less than 10 ppm, or less than 20 ppm, or less than 50 ppm, or less than 100 ppm of the target metal. Preferably the barren solution contains between about 0.001 and 100 ppm, or between about 0.001 and 50 ppm, or between about 0.001 and 50 ppm, or between about 0.01 and 50 ppm of the target metal. In particular embodiments, the pregnant aqueous solution contains at least 10 times more target metal than the barren solution. Preferably the pregnant aqueous solution contains at least 20 times, or at least 40 times, or at least 45 times, or at least 50 times more target metal than the barren solution.

It is acknowledged that the microorganism may be cultivated in a separate vessel or vessels by any methods familiar to those skilled in the art prior to contacting with the pregnant aqueous solution in biosorption vessel 1. By way of example, a microorganism can be cultivated in a bioreactor (not shown) containing suitable growth media and transferred to biosorption vessel 1. The microorganism may be concentrated prior to transfer or passed directly without further concentration. In certain embodiments, the microorganism is concentrated through gravity separation and passed to biosorption vessel 1 as a concentrated microorganism slurry in a minimal volume of growth media. In a related embodiment, the concentrated microorganism slurry may be washed in another solution prior to being passed to biosorption vessel 1.

In certain embodiments, the microorganism is cultivated in rich liquid media (e.g. nutrient broth or tryptic soy broth) until the mid-log or stationary phase of growth is reached.

Referring to FIG. 1, upon at least partial biosorption of the target metal, the metal laden microorganism is separated from the barren solution in separation module 3. It is anticipated that the initial part of the separation step may occur in the same vessel as the biosorption step, wherein the metal laden microorganism is simply allowed to concentrate via gravity separation. In other embodiments, the metal laden microorganism and barren solution are passed to a separation module 3 via conduit means 2 for separation. Examples of means to separate a microorganism from a barren solution will be familiar to those skilled in the art. However, by way of example, the metal laden microorganism may be separated by gravity separation, centrifugation, filtration or a combination thereof such that in each case the barren solution is removed from the metal laden microorganism.

Reference to substantially separating should be taken to mean physically separating at least a portion of the barren solution from the metal laden microorganism. Physically separating refers to having them in separate non-touching locations, for example separate containers rather than touching layers within the same container.

In particular embodiments, the metal laden microorganism gravity separate from the barren solution over a time period in biosorption vessel 1 or separation module 3. Following gravity separation, at least a portion of the barren solution can be decanted, syphoned or otherwise removed leaving the concentrated metal laden microorganism which can be passed to recovery module 5 to carry out the recovery step.

In certain embodiments, the separating step comprises gravity separation of the metal laden microorganism from the barren solution, wherein at least 50% of the barren solution is removed. Preferably at least 60%, or at least 70%, or at least of 80%, or at least 90%, or at least 95% of the barren solution is removed. By way of example, a solution of the microorganism may be left to sediment by gravity for up to 2 hours, or up to 6 hours, or up to 12 hours, or up to 24 hours, or up to 48 hours, or up to 72 hours before removing the barren solution.

In an alternative embodiment, the metal laden microorganism can be separated from the barren solution in separation module 3 by centrifugation and removal the barren solution. Those familiar with the art will recognise the appropriate conditions and equipment necessary for separating the barren solution from the metal laden microorganism, which following separation can be passed to recovery module 5 via conduit means 4.

In certain embodiments, the separating step comprises separating the metal laden microorganism by centrifugation, wherein during the centrifugation at least 50% of the barren aqueous is removed from the metal laden microorganism. Preferably at least 60%, or at least 70%, or at least of 80%, or at least 90%, or at least 95% of the barren solution is removed during centrifugation.

Those skilled in the art will recognise operation of a centrifuge will be dependent on the volumes of liquid addressed and the rate of separation required. There are also a number of centrifuge systems that may be employed with the methods and systems of the invention including suitable continuous flow centrifugation or decanter centrifuge device.

In a further embodiment, the metal laden microorganism can be separated from the barren solution in the separation module 3 by filtration. Those familiar with the art will recognise the appropriate conditions and equipment necessary for separating the barren solution from the metal laden microorganism, which following separation can be passed to recovery module 5 via conduit means 4.

In certain embodiments, the separating step comprises separating the metal laden microorganism by filtration, wherein during the filtration at least 50% of the barren solution is removed from the metal laden microorganism Preferably at least 60%, or at least 70%, or at least of 80%, or at least 90%, or at least 95% of the barren solution is removed during filtration.

As an example, solutions containing the metal laden microorganism may be filtered under vacuum through filters with pore size of approximately 0.45 μm or approximately 0.65 μm or approximately 0.8 μm or approximately 1 μm to remove barren solution. As another example, a cross flow filtration device or membrane bioreactor device may be used to remove the barren solution.

The separating step is important for a number of reasons. The separating step removes the metal laden microorganisms, and therefore the metal, from the other components in the pregnant solution. The other components in the pregnant can be toxic or corrosive, such as cyanide or acids. The separation step also allows for the concentration of the target metal. Following the separation step the dried metal laden microorganisms preferably include greater than 100 ppm, or greater than 200 ppm, or greater than 500 ppm or greater than 1000 ppm or greater than 30.00 ppm of the target metal. Further the inventors have shown significant concentration factors of the target metal from the pregnant solution to the separated microorganism. The concentration factor of the target metal from the pregnant aqueous solution to the microorganism (i.e. the number of times more concentrated target metal is in the microorganism over the pregnant solution) is greater than 5 or greater than 10, or greater than 20, or greater than 50, or greater than 100, or greater than 900. For example, Example 1 shows a concentration factor of the target metal from the pregnant solution to the microorganism of 990. Wet microorganism biomass is commonly estimated to be five-fold that of its dry mass, i.e. dry mass is ~20% of wet mass (Luria, The Bacteria, vol. 1. Academic Press, Inc., New York, pp 1-34 (1960)). It therefore follows that metal concentration factors calculated for wet microorganism biomass, as used in Examples 1 and 5, can be multiplied five-fold to estimate concentration factors for the dry microorganism. Drying of the microorganism is exemplified in Example 8. This concentration is important as, for example, although lixiviants are used in hydrometallury to extract metal the metal must still be recovered from the lixiviant.

The separation step can in some cases also allow for selective separation and/or concentration of metals, for example, Example 7 demonstrates preferential biosorption and then separation and/or concentration of gold from copper. The gold selectively biosorbs to the microorganisms, so that in the separating step the gold which is biosorbed to the microorganism is separated from the copper in the barren solution.

Those familiar with the art will recognise suitable recovery means for recovering target metal from the metal laden microorganism in recovery module 5. However, by way of non-limiting example, the metal may be desorbed from the metal laden microorganism by altering the conditions of the microorganism. For example in certain embodiments of the invention, the metal may be desorbed from the metal laden microorganism by altering the pH of the microorganism, for example by contacting the microorganisms with a solution that contains an acid or a base. In such an embodiment, the microorganism would be contacted with a liquid with a particular pH to elicit desorption of the target metal into the liquid. In particular embodiments, the pH of the contacted liquid is higher pH than the barren solution while in other embodiments the pH is lower—depending on the characteristics of the system.

By way of example, the conditions may be of pH less than 5, or pH less than 4, or pH less than 3, or pH less than 2. By way of further example, the conditions may be of pH greater than 8, or pH greater than 9, or pH greater than 10, or pH greater than 11, or pH greater than 12.

In an alternative embodiment, the metal laden microorganism may be contacted with a liquid containing a compound to elicit desorption of the target metal into the liquid. By way of example, aqueous cysteine may be used in certain embodiments to elicit the desorption of the target metal. In certain embodiments wherein the target metal is gold, approximately 0.3 mM, or approximately 1 mM, or approximately 10 mM, or approximately 30 mM, or approximately 60 mM cysteine solutions may be contacted with the metal laden microorganism (Kenney et al, *Geochimica et Cosmochimica Acta* 82, pp 51-60 (2012)). In a related embodiment, aqueous thiosulphate, thiourea, thiocyanate, cyanide or other thiol ligands may be used to elicit desorption of gold from the microorganism. As shown in Example 10, chlorine gas can be used to alter the conditions. Additionally or alternatively, other conditions such as a change in oxidation-reduction potential or temperature may be used to promote desorption of the target metal.

The concentrated solutions may then be subjected to separation and purification procedures such as precipitation of impurities, solvent extraction, adsorption and ion-exchange to isolate and/or further concentrate the target metal. Subsequently, the solutions can be treated by electrorefining process, chemical reduction, or crystallization for target metal recovery or other methods that those skilled in the art will be aware of.

In an alternative embodiment, the separated metal laden microorganism may be dried and burnt to recover the target metal, which may be separated from the ash using conventional pyrometallurgy or hydrometallurgy techniques known to those skilled in the art (Hennebel et al, *New Biotechnology* 32, pp 121-127 (2015)).

It will be apparent that the recovery step can recover the target metal in metallic or ion form. Reference to recovering the target metal should therefore be taken to include recovery of metallic metal or metal ions.

In particular embodiments of the methods and systems of the invention, the target metal is gold. In such embodiments, the separated gold laden microorganism may be dried at ambient temperature or 30° C. or 50° C. to minimise water content and then incinerated, for example by gas torch, gently so as to minimise the loss of ash generated. This ash may then be treated with nitric acid to solubilise base metals, filtered, and the gold-containing residue treated with aqua regia (1 part nitric acid to 3 parts hydrochloric acid) to generate a solution of chloroauric acid. In a related embodiment, the gold laden microorganism may directly undergo the aforementioned acid treatment without requiring prior incineration. Gold may be precipitated and smelted from chloroauric acid using methods known to those with ordinary knowledge of the art.

According to another aspect of the invention, there is provided a method of recovering a target metal, the method comprising:

(a) a dissolution step comprising dissolving target metal from a solid feedstock material with a lixiviant to form a pregnant aqueous solution containing the target metal;

(b) a biosorption step comprising contacting a microorganism with the pregnant aqueous solution such that at least a portion of the target metal ions biosorb to the microorganism wherein the microorganism become metal laden, and pregnant aqueous solution becomes barren;

(c) a separating step comprising substantially separating the metal laden microorganism from the barren solution; and (d) a recovery step comprising recovery of the target metal from the metal laden microorganism.

Figure 2:
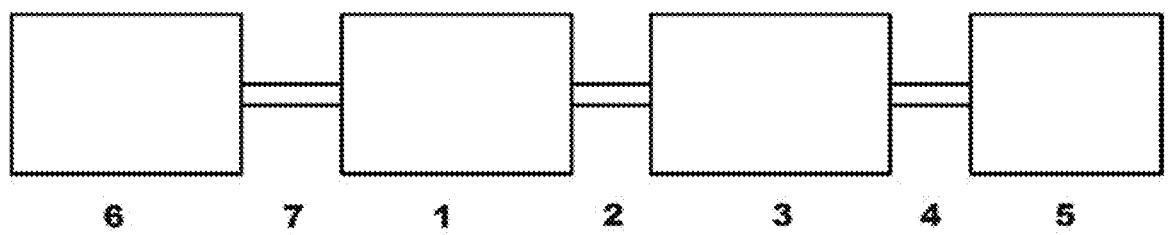
FIG. 2 represents a system configured for recovering target metal from a solid feedstock material in accordance with the fifth aspect of the invention.

Referring to FIG. 2, a target metal may be selectively dissolved from a solid feedstock material in dissolution vessel 6, by contacting with an appropriate lixiviant. Those skilled in the art will appreciate suitable lixiviants for selectively dissolving particular target metals. By way of non-limiting example, when gold is the target metal the lixiviant may be selected from a thiourea-based solution, or a thiosulphate-based solution, or a thiocyanate-based solution, or a cyanide-based solution, or a halogen-based solution, or an aqua regia-based solution, and examples of suitable conditions can be found in Aylmore, *Developments in Mineral Processing* 15, pp 501-539 (2005).

In particular embodiments, the solid feedstock material is contacted with the lixiviant for a time period necessary to dissolve at least 50% of the target metal, or at least 60% of the target metal, or at least 70% of the target metal, or at least 80% of the target metal, or at least 90% of the target metal, or at least 95% of the target metal to produce a pregnant aqueous solution. In particular embodiments, the solid feedstock material/lixiviant mixture may need to be gently heated to over 30° C., or over 40° C. or over 50° C. to assist with dissolution. Similarly, the mixture may be agitated, sonicated, vibrated or otherwise treated to assist with dissolution.

The solid feedstock material may be any material comprising target metal residues. By way of example, the solid feedstock material may comprise metal ore, sands, clays, residues or waste materials bearing the target metal. By way of non-limiting example, in certain embodiments of the invention wherein the target metal is gold, the solid feedstock material is gold ore extracted from the gold mining process or printed circuit boards from e-waste. In certain embodiments the solid feedstock material may be at least partially or completely ground prior to contacting with the lixiviant. However, this may not always be necessary in all cases such as embodiments where the target metal is surface coated on the solid feedstock material.

In certain embodiments the solid feedstock material comprises a solid material comprising less than 5%, or less than 1%, or less than 0.1%, or less than 0.01%, or less than 0.001%, or less than 0.0001% of target metal. In particular embodiments, the target metal is gold.

In certain embodiments wherein the solid feedstock material is gold ore or e-waste gold the lixiviant may be selected from a thiourea-based solution, or a thiosulphate-based solution, or a thiocyanate-based solution, or a cyanide-based solution, or a halogen-based solution, or an aqua regia-based solution, and examples of suitable conditions can be found in Aylmore, *Developments in Mineral Processing* 15, pp 501-539 (2005).

Referring to FIG. 2, upon at least partial dissolution of the target metal in the lixiviant in dissolution vessel 6, the pregnant aqueous solution is passed to biosorption vessel 1 via conduit means 7, wherein the previously described biosorption-separation-recovery process can be completed. Those skilled in the art will recognise dissolution vessel 6 and biosorption vessel 1 may be the same vessel or different vessels depending on the methods and conditions used. In particular embodiments of the invention, the dissolution vessel 6 and biosorption vessel 1 are separate vessels.

Unless indicated otherwise, the order of steps described in the methods described herein is very much preferred and has been optimised by trials carried out by the inventors to ensure that the process provides an efficient yield and an economically viable recovery method.

EXAMPLES

Example 1 Biosorption of Gold Dissolved in Aqua Regia

Materials and Methods:
Microorganism cultures were grown under aseptic conditions, but subsequent processing took place using non-sterile solutions and equipment.
1. 25 mL of nutrient broth (0.5% peptone, 0.3% yeast extract) was inoculated with *Cupriavidus metallidurans* strain CH34 (Deutsche Sammlung von Mikroorganismen und Zellkulturen GmbH #2839) and grown for at least 16 hours to stationary phase at 30° C., ~200 rpm.
2. The culture was centrifuged at 3,100 rcf for 15 minutes, the supernatant discarded, and the pellet (~0.1 g) resuspended in 30 mL of 0.1 M sodium perchlorate to wash. This centrifuge/wash step was repeated again with a 10 mL volume.
3. The culture was centrifuged again as above, the supernatant discarded, and the pellet resuspended in 25 mL of 0.1 M sodium perchlorate, 25 µM chloroauric acid (~5 ppm Au), pH 4 (adjusted with sodium hydroxide) (pregnant solution). The pH of the gold/microorganism mixture was checked and adjusted to 4.0-4.5 using sodium hydroxide or hydrochloric acid as necessary.
4. The gold/microorganism mixture was incubated at room temperature for 2 hours. To keep the microorganism in suspension, the mixture was gently agitated on an orbital shaker throughout.
5. The mixture was centrifuged as per step 2, the supernatant (barren solution) discarded, and the pellet stored at 4° C.
6. The pellet (biosorption pellet) from step 5 (approximately 100 µL volume) was resuspended in 100 mL water, 1 mL of 70% nitric acid added, and then analysed for total gold content by inductively coupled plasma mass spectrometry (service provided by Watercare Services Ltd, Auckland, New Zealand).

Results:
At the end of the biosorption period (step 4), the pH of the mixture was checked, and was found to be between 4.5-5.0.

Total gold content was reported as mg/L based on the volume submitted for analysis, and used to calculate the amount biosorbed and biosorption yield (Table 1). Precision of total gold content was estimated at 15-20% variance.

TABLE 1

| Sample | Au input (mg) | Au content reported from step 6 (mg/L [ppm]) | Au biosorbed (mg) | Yield (% Au input) |
|---|---|---|---|---|
| *C. metallidurans* biosorption pellet | 0.125 | 0.990 | 0.099 (0.990 mg/L × 0.1 L) | 79 |

Based on the amount of gold biosorbed, the pregnant solution contained about 4 times more target metal (gold) than the barren solution.

Using the data in Table 1, the concentration of gold left in the barren supernatant was backcalculated to be ~1 ppm ([0.125 mg-0.099 mg]/0.025 L). The concentration factor from the biosorption process was also calculated using the original biosorption pellet volume of ~100 µL (Table 2), i.e. the increase in concentration of Au from the pregnant solution to the biosorption pellet (wet microorganism). Wet microorganism biomass is commonly estimated to be five-fold that of its dry mass, i.e. dry mass is ~20% of wet mass (Luria, The Bacteria, vol. 1. Academic Press, Inc., New York, pp 1-34 (1960)). Therefore this approximates to a concentration factor for Au of about 990 from the pregnant solution to dry microorganism.

TABLE 2

| Sample | Au input solution concentration (mg/L [ppm]) | Au output pellet slurry concentration (mg/L [ppm]) | Increase in Au concentration to wet biomass (Concentration Factor) |
|---|---|---|---|
| *C. metallidurans* biosorption pellet | 5 | 990 (0.099 mg ÷ 0.0001 L initial volume of pellet) | 198 |

Example 2 Biosorption and Desorption of Gold Chloride

Materials and Methods:
Microorganism cultures were grown under aseptic conditions, but subsequent processing took place using non-sterile solutions and equipment.
1. 600 mL of tryptic soy broth (1.7% tryptone, 0.3% soytone, 0.25% glucose, 0.5% sodium chloride, 0.25% dipotassium phosphate) was inoculated with either *Bacillus subtilis* strain (Ehrenberg 1835) Cohn 1872 (Landcare Research New Zealand Ltd #20567) or *Pseudomonas putida* strain (Trevisan 1889) Migula (Landcare Research New Zealand Ltd #15057) and grown for at least 16 hours to stationary phase at 30° C., ~200 rpm.

2. Each culture was centrifuged at 2,500 rcf for 10 minutes, the supernatant discarded, and the pellet resuspended in 300 mL of water. This centrifuge/wash step was repeated a second time.
3. Each culture was centrifuged again as above, the supernatant discarded, and the pellet resuspended in 20 mL of 0.1 M sodium perchlorate. This centrifuge/wash step was repeated a second time.
4. Each culture was centrifuged again as above, the supernatant discarded, and the wet mass of the pellet weighed. Each pellet was resuspended in 0.1 M sodium perchlorate to give a 250 g/L concentration.
5. To 117.5 mL of 25 µM chloroauric acid (~5 ppm Au) pH 4 (adjusted with sodium hydroxide) (pregnant solution), 2.4 mL of 250 g/L microorganism solution was added to give a final concentration of ~5 g/L microorganism in 120 mL. This was performed separately for both *B subtilis* and *P. putida*. The pH of the gold/microorganism mixture was checked and adjusted to 3.0-4.0 using sodium hydroxide or hydrochloric acid as necessary.
6. Each gold/microorganism mixture was incubated at 30° C. for 2 hours. To keep the microorganism in suspension, each mixture was gently agitated on an orbital shaker throughout.
7. Each mixture was centrifuged as per step 2, and the supernatant (barren solution) decanted and stored at 4° C.
8. Each pellet was resuspended in 7 mL of supernatant, 0.11 g of L-cysteine hydrochloride monohydrate was added, and the pH adjusted with 1 M NaOH to 7.9-8.1. Each mixture was topped up with supernatant to a final volume of 10 mL, giving a cysteine concentration of ~62 mM.
9. Each cysteine/gold/microorganism mixture was incubated at 30° C. for 2 hours as per step 6.
10. Each mixture was centrifuged as per step 2, and the supernatant decanted. Both the supernatant and pellet were stored at 4° C.
11. The following *B. subtilis* and *P. putida* samples were analysed for total gold content by inductively coupled plasma mass spectrometry (service provided by Watercare Services Ltd, Auckland, New Zealand):
    a. Barren supernatant (step 7): 100 mL with 1 mL of 70% nitric acid added.
    b. Desorption supernatant (step 10): 7 mL made up to 100 mL with water (~14.3×dilution), 1 mL of 70% nitric acid added.

Results:

The wet mass of washed pellet from 600 mL of *B. subtilis* culture was 3 g, and was therefore resuspended in 12 mL 0.1 M sodium perchlorate to give a 250 g/L concentration; for *P. putida*, the mass and resuspension was 2.6 g and 10.4 mL respectively.

At the end of the biosorption period (step 6), the pH of each mixture was checked, and was found to be between 3.0-4.0.

Total gold content was reported as mg/L based on the volume submitted for analysis, and used to calculate the amount biosorbed or desorbed, and the yield when compared to the gold input mass (Table 3). Precision of total gold content was estimated at 15-20% variance.

TABLE 3

| Sample | Au input (mg) | Au content reported from step 11 (mg/L [ppm]) | Au content (mg) | Yield (% Au input) |
|---|---|---|---|---|
| *B. subtilis* barren supernatant | 0.588 | 0.098 | 0.012 (0.098 mg/L × 0.12 L) | 2 (98% biosorbed) |
| *B. subtilis* desorption supernatant | 0.588 | 0.360 | 0.052 (0.36 mg/L × 14.3 dilution × 0.01 L) | 9 (91% still biosorbed) |
| *P. putida* barren supernatant | 0.588 | 0.300 | 0.036 (0.300 mg/L × 0.12 L) | 6 (94% biosorbed) |
| *P. putida* desorption supernatant | 0.588 | 4.400 | 0.629 (4.400 mg/L × 14.3 dilution × 0.01 L) | 107 (0% still biosorbed) |

For *B. subtilis* the pregnant solution contained about 49 times more target metal than the barren solution. For *P. putida* the pregnant solution contained about 16 times more target metal than the barren solution.

The results in Table 3 show both *B. subtilis* and *P. putida* biosorbed greater than 90% of the gold from the pregnant solution. Following the recovery step (steps 8-10) it was found *P. putida* readily desorbed the gold using cysteine conditions. *B. subtilis* less readily released the gold using cysteine conditions, although it is believed other conditions could be used to increase the recovery rate if required.

Using these results, the concentration factor from the biosorption process was calculated using the desorption supernatant volume of 10 mL (Table 4). In this Example the concentration factor is the change in concentration from the pregnant solution to the recovered Au (i.e. the desorption supernatant). The lower value for *B. subtilis* is due to the lower desorption rate discussed above, rather than the biosorption step.

TABLE 4

| Sample | Au input concentration (mg/L [ppm]) | Au output concentration (mg/L [ppm]) | Increase in Au concentration (Concentration factor) |
|---|---|---|---|
| *B. subtilis* | 5 | 5.2 (0.052 mg ÷ 0.01 L) | 1.0 |
| *P. putida* | 5 | 62.9 (0.629 mg ÷ 0.01 L) | 12.6 |

Example 3: Gold Dissolving Lixiviants

Materials and Methods:

A sample of gold-bearing quartz ore (milled to <100 µm particle size), containing ~16 ppm Au and ~260 ppm Ag, was obtained from a mine working from the Coromandel region, New Zealand. Printed circuit boards were collected from discarded desktop computers, and sections with gold-plated connector pins were cut from the boards and used as a model e-waste feedstock.

1. Lixiviant solutions for gold were made as per the following:
    a. Thiosulphate-based lixiviant: 0.2 M sodium thiosulphate pentahydrate, 0.4 M ammonia, 12 mM copper sulphate pentahydrate; pH adjusted to 9.5-10.0 using 1 M sulphuric acid.

b. Thiourea-based lixiviant: 0.13 M thiourea, 5 mM iron (III) chloride; pH adjusted to 1.0-1.5 using 1 M sulphuric acid.
2. In separate 500 mL flat-bottomed glass bottles for each feedstock/lixiviant combination, 100 mL of lixiviant was added to each of the following gold feedstocks:
    a. 2 to 20 mg gold powder
    b. 25 g milled ore (containing ~0.4 mg Au)
    c. Two ~0.5 cm$^2$ gold-plated pin sections of e-waste
3. Reactions were incubated at 30° C., ~100 rpm for 20 hours. The lids of the bottles were kept loose to allow air exchange.
4. Reactions were allowed to stand (to let milled ore solids sediment), and pregnant lixiviant decanted. The following samples were analysed for total gold content by inductively coupled plasma mass spectrometry (service provided by Watercare Services Ltd, Auckland, New Zealand):
    a. Gold powder (thiosulphate-based lixiviant): 20 mL made up to 100 mL with water (2× dilution), 1 mL of 70% nitric acid added.
    b. Gold powder (thiourea-based lixiviant): 10 mL made up to 100 mL with water (2× dilution), 1 mL of 70% nitric acid added.
    c. Milled ore (thiosulphate-based lixiviant): 50 mL made up to 100 mL with water (2× dilution), 1 mL of 70% nitric acid added.
    d. Milled ore (thiourea-based lixiviant): 50 mL made up to 100 mL with water (2× dilution), 1 mL of 70% nitric acid added.
    e. E-waste (thiosulphate-based lixiviant): 50 mL made up to 100 mL with water (2× dilution), 1 mL of 70% nitric acid added.

Results:

For the thiosulphate-based lixiviant, the initial oxidation-reduction potential was measured to be between 230 and 260 mV (with respect to a standard hydrogen electrode); at the end of leaching, this was between 160 and 180 mV. For the thiourea-based lixiviant, these values were between 360-400 mV and 340-370 mV respectively. The starting colour of the thiosulphate-based lixiviant was light blue, changing to dark blue by the end of leaching.

The starting colour of the thiourea-based lixiviant was pale orange, changing to colourless by the end of leaching (with white precipitate forming).

The dissolution of gold powder in lixiviant could be observed; for milled ore, no apparent change was obvious; while for the e-waste, discolouration and dissolution of gold plating could be observed. E-waste was not trialled with the thiourea-based lixiviant, although there is no reason to believe it would not give a similar result to the other feedstocks listed. Total gold content was reported as mg/L based on the volume submitted for analysis, and used to calculate the amount leached from the feedstock, and the yield compared to the gold input mass where applicable (Table 5). Precision of total gold content was estimated at 15-20% variance.

TABLE 5

| Sample | Au input (mg) | Au content reported (mg/L [ppm]) | Au leached (mg) | Yield (%) Au input) |
|---|---|---|---|---|
| Gold powder (thiosulphate lix.) | 18.800 | 28.000 | 14.000 (28.000 mg/L × 5 dilution × 0.1 L) | 75 |
| Gold powder (thiourea lix.) | 3.200 | 3.400 | 3.400 (3.400 mg/L × 10 dilution × 0.1 L) | 106 |
| Milled ore (thiosulphate lix.) | 0.400 | 1.300 | 0.260 (1.300 mg/L × 2 dilution × 0.1 L) | 65 |
| Milled ore (thiourea lix.) | 0.400 | 0.990 | 0.198 (0.990 mg/L × 2 dilution × 0.1 L) | 50 |
| E-waste (thiosulphate lix.) | 0.625* | 2.3 | 0.460 (2.300 mg/L × 2 dilution × 0.1 L) | 74* |

Lix., lixiviant;
*e-waste Au input estimated.

Example 4: Chlorine Lixiviant

Materials and Methods:

As a model e-waste feedstock, printed circuit boards were collected from discarded desktop computers and sections with gold-plated connector pins were cut from the boards.
1. Five ~1 cm$^2$ gold-plated pin sections of e-waste (1.21 g total mass) were placed in a flat-bottomed reaction flask, and 100 mL of water added. The flask was placed on a magnetic stirring plate, and a stirring flea added. Stirring took place at a speed suitable to keep the e-waste moving around the flask.
2. Chlorine gas was slowly sparged into the reaction liquid to form a chlorine-based lixiviant.
    a. Chlorine gas was generated by dripping 12 mL of 32% hydrochloric acid onto 3 g of potassium permanganate in a separate flask at 9 ml/hour using a syringe pump.
    b. Excess chlorine gas from the e-waste reaction flask was allowed to escape via sparging into 50 mL of a 7 mM sodium thiosulphate pentahydrate solution in order to neutralise.
3. After 7 hours, the reaction was observed to be complete, and the pregnant lixiviant was decanted into a separate flask.
4. 5 mL of the pregnant lixiviant was sent for analysis for total gold content by inductively coupled plasma mass spectrometry (service provided by University of Auckland Mass Spectrometry Centre, Auckland, New Zealand).

Results:

Total gold content was reported as mg/L based on the volume submitted for analysis, and used to calculate the amount leached from the feedstock (Table 6). Precision of total gold content was estimated at 15-20% variance.

TABLE 6

| Sample | Au content reported (mg/L [ppm]) | Au leached (mg) | Au proportion of entire e-waste mass (%) |
|---|---|---|---|
| E-waste (chlorine lixiviant) | 94.880 | 9.488 (94.880 mg/L × 0.1 L) | 0.8 (9.488 mg ÷ 1.21 g e-waste) |

While the amount of gold leached from the feedstock is relatively low as a percentage of the whole mass of the e-waste, this reflects the amount of gold available for leaching; 0.8% is equivalent to 8,000 ppm on a mass basis, which is a high concentration to those skilled in the art.

Example 5: Biosorption from Chlorine Solution

Materials and Methods:

Microorganism cultures were grown under aseptic conditions, but subsequent processing took place using non-sterile solutions and equipment.

Chlorine-based lixiviant that was pregnant with gold from an e-waste feedstock was generated as per Example 4.

1. 25 mL of *Cupriavidus metallidurans* strain CH34 was cultured as per Example 1.
2. The culture was centrifuged at 4,000 rcf for 12 minutes, the supernatant discarded, and the pellet (~0.1 g) resuspended in 30 mL of 0.85% saline solution to wash. This centrifuge/wash step was repeated a second time.
3. The culture was centrifuged again as above, and the supernatant discarded.
4. 30 mL of chlorine-based lixiviant pregnant with gold from an e-waste feedstock (~95 ppm Au) was sparged gently with air for 45 minutes to drive off remaining chlorine gas, and the pH adjusted to 4.5-5.0 with sodium hydroxide. This solution was then used to resuspend the microorganism pellet from step 3.
5. The gold/microorganism mixture was incubated at room temperature for 22 hours. To keep the microorganism in suspension, the mixture was gently agitated on an orbital shaker throughout.
6. The mixture was centrifuged as per step 2, and the supernatant decanted and stored at 4° C. The pellet was resuspended in 30 mL of water to wash and centrifuged as per step 2.
7. The supernatant was discarded, and the pellet resuspended in 2 mL water. This was stored at 4° C.
8. The following samples were analysed for total gold content by inductively coupled plasma mass spectrometry (service provided by University of Auckland Mass Spectrometry Centre, Auckland, New Zealand):
    a. Barren supernatant (step 6): 5 mL.
    b. Biosorption pellet (step 7): 1 mL.

Results:

Total gold content was reported as mg/L based on the volume submitted for analysis, and used to calculate the amount biosorbed and biosorption yield (Table 7). Precision of total gold content was estimated at 15-20% variance.

TABLE 7

| Sample | Au input (mg) | Au content reported (mg/L [ppm]) | Au biosorbed (mg) | Yield (% Au input) |
|---|---|---|---|---|
| *C. metallidurans* barren supernatant | 2.850 | 48.650 | 1.46 (48.65 mg/L × 0.03 L)) | 51 (49% biosorbed) |
| *C. metallidurans* biosorption pellet | 2.850 | 656.900 | 1.314 (656.9 mg/L × 0.002 L) | 46 |

The pregnant solution contained about 2 times more target metal than the barren solution. Using these results, the concentration factor from the biosorption process was calculated (Table 8), i.e. the increase in concentration of Au from the pregnant solution to the wet biosorption pellet. This approximates to a concentration factor of about 34.5 for the Au from the pregnant solution to dry biomass.

TABLE 8

| Sample | Au input concentration (mg/L [ppm]) | Au output concentration (mg/L [ppm]) | Increase in Au concentration (Concentration factor) |
|---|---|---|---|
| *C. metallidurans* | 95 | 657 | 6.9 |

Example 6: Separating Laden Microorganism from Barren Solutions

Materials and Methods:

Microorganism cultures were grown under aseptic conditions, but subsequent processing took place using non-sterile solutions and equipment.

As an example, gold/microorganism mixtures were prepared as per Example 6.

1. To separate the gold laden microorganism from barren lixiviant solution, samples were processed by either centrifugation or filtering:
    a. Centrifugation: mixtures were centrifuged at 3,000 to 8,000 rcf for at least 10 minutes, and the barren lixiviant supernatant decanted from the gold laden microorganism pellet. For washing, the pellet was resuspended in a volume of wash solution, and subsequently recovered through another centrifugation step.
    b. Filtering: mixtures were applied to 0.45 μm PVDF filters under ~20 cm Hg vacuum for several minutes until all liquid had passed through. The filtrate was barren lixiviant, and the residue the gold laden microorganism. For washing, a volume of wash solution was added to the residue and filtered through under vacuum. Residue was recovered by washing the filter in a 50 mL Falcon tube with a volume of wash solution until the gold laden microorganism was resuspended, and the filter subsequently discarded.

Results:

Both centrifugation or filtration served adequately to separate barren lixiviant solution from the gold laden microorganism.

Example 7: Preferential Biosorption of Gold from Gold/Copper Solution

Materials and Methods:

Microorganism cultures were grown under aseptic conditions, but subsequent processing took place using non-sterile solutions and equipment.

1. 120 mL of *Cupriavidus metallidurans* strain CH34 was cultured as per Example 1.
2. The culture was split into 6 equal aliquots, centrifuged at 4,350 rcf for 10 minutes, the supernatant discarded, and the pellets resuspended in 30 mL of 0.85% saline solution to wash. This centrifuge/wash step was repeated a total of 2 times, with the final wash supernatant discarded.
3. Pellets (averaging 0.15 g wet weight) were resuspended in 30 mL of a 2-fold chloroauric acid serial dilution, ranging from 325 μM (~64 ppm) to 10 μM (~2 ppm) chloroauric acid made up in 0.85% saline solution at an original adjusted pH of 5.5.

4. Copper chloride was also added to each dilution sample prior to pellet resuspension to a final concentration of 32.5 mM (2,060 ppm).
5. The gold/copper/microorganism mixture was incubated at room temperature for 4 hours. To keep the microorganism in suspension, the mixture was gently agitated on an orbital shaker throughout.
6. The mixture was centrifuged as per step 2, and the supernatant set aside. Pellets were resuspended/washed with water as per step 2, and finally resuspended in 1.2 mL water (total volume estimated at 1.3 mL).
7. Half (0.65 ml) of each sample from step 6 was digested in 4 mL of acid mix (3 mL 69% nitric acid, 1 mL) and then analysed for total gold and copper content by inductively coupled plasma mass spectrometry (service provided by University of Auckland Mass Spectrometry Centre, Auckland, New Zealand).

Results:

Total metal content was reported as mg/L based on the volume submitted for analysis, and used to calculate the amount biosorbed and biosorption yield (Table 9). Precision of total gold content was estimated at 15-20% variance.

TABLE 9

| Sample | Metal input (mg) | Metal content reported (mg/L [ppm]) | Metal biosorbed (mg) | Yield (% metal input) | Change in mass ratio Au:Cu from input to biosorbed (factor of change in mass ratio) |
| --- | --- | --- | --- | --- | --- |
| 325 µM Au | 1.92 Au | 177.1 Au | 1.65 Au | 84.4% Au | 1:32 to 9:1 |
|  | 62 Cu | 20.0 Cu | (177.1 mg/L × 0.00465 L × 2) 0.19 Cu | 0.3% Cu | (288 increase) |
| 163 µM Au | 0.96 Au | 109.6 Au | 1.02 Au | 106% Au | 1:62 to 5:1 |
|  | 62 Cu | 18.4 Cu | 0.17 Cu | 0.3% Cu | (310 increase) |
| 81 µM Au | 0.48 Au | 81.8 Au | 0.76 Au | 158% Au | 1:124 to 4:1 |
|  | 62 Cu | 22.9 Cu | 0.21 Cu | 0.3% Cu | (496 increase) |
| 41 µM Au | 0.24 Au | 41.5 Au | 0.39 Au | 163% Au | 1:258 to 1:1 |
|  | 62 Cu | 32.8 Cu | 0.30 Cu | 0.5% Cu | (258 increase) |
| 20 µM Au | 0.12 Au | 21.2 Au | 0.20 Au | 167% Au | 1:517 to 1:2 |
|  | 62 Cu | 38.2 Cu | 0.35 Cu | 0.6% Cu | (259 increase) |
| 10 µM Au | 0.06 Au | 10.4 Au | 0.10 Au | 167% Au | 1:1033 to 1:3 |
|  | 62 Cu | 32.2 Cu | 0.30 Cu | 0.5% Cu | (344 increase) |

This shows a microorganism (in this case *C. metallidurans*) can selectively biosorb metals. In this case gold was very selectively biosorbed over copper. This allows metals to be selectively separated in a separating step, i.e. separating the metal laden microorganism from the barren solution. In this case the gold laden microorganism can be separated from the barren solution which retained much of the copper.

It can be seen from Table 9 that the mass ratio of gold to copper changes after biosorption. For example, in the sample "325 µM Au", the gold to copper ratio in the metal input is approximately 1:32; after biosorption, the ratio is found to be approximately 9:1 in favour of gold. This results in a 288-fold increase in the mass ratio. In a similar manner for the sample "10 µM Au", the gold to copper ratio increases from 1:1,000 to 1:3, an enrichment of over 300-fold with respect to copper.

Example 8: Preferential Biosorption of Gold from Gold/Copper/Nickel Solution and Drying of Metal-Laden Microorganism Materials and Methods:
1. 84 g of wet *C. metallidurans* biomass (generated in a similar manner to Example 5) was contacted with 250 mL of lixiviant solution pregnant with gold, copper and nickel (generated from leaching e-waste in a similar manner to Example 4) at 22° C. for 2.25 hours under gentle agitation.
2. The mixture was centrifuged for 40 minutes at 4,000 rcf in centrifuge jars, and the supernatant set aside. Pellets were resuspended in 1.1 L water to wash and centrifuged as above, and the wash supernatant set aside.
3. The pelleted metal-laden biomass was spread on trays and allowed to dry over 72 hours, giving a dry mass of approximately 22 g.
4. 125 mg of this dry biomass was ground, digested in 4 mL aqua regia, and analysed for total gold, copper and nickel content by atomic absorption spectrometry using a Shimadzu AA-6300 (Shimadzu Corp, Kyoto, Japan) as per the manufacturer's instructions.

Results:

Total metal content was reported as mg/L and used to calculate the amount of each metal biosorbed and biosorption yield (Table 10). Accuracy of total metal content was estimated at 15-20% variance.

TABLE 10

| Sample | Metal input (mg) | Metal content reported (mg/L [ppm]) | Metal mass contained (mg) | Yield (% metal input) | Change in mass ratio Au:Cu and Au:Ni from input to biosorbed (factor of change in mass ratio) |
|---|---|---|---|---|---|
| Pregnant lixiviant (250 mL) | — | 3,589.3 Au 527.8 Cu 68.2 Ni | 897.3 Au (3,589.3 mg/L × 0.25 L) 132.0 Cu 17.1 Ni | — | — |
| *C. metallidurans* dried biomass (125 mg) | 5.09 Au (897.3 mg × [0.125 g/22 g]) 0.75 Cu 0.10 Ni | 1,132.7 Au 52.7 Cu 2.6 Ni | 4.53 Au (1,132.7 mg/L × 0.004 L) 0.21 Cu 0.01 Ni | 89.0% Au 28.0% Cu 10.0% Ni | Au:Cu 7:1 to 22:1 (3) Au:Ni 51:1 to 453:1 (9) |
| *C. metallidurans* dried biomass (extrapolated to 22 g total dried biomass) | 897.3 Au* 132.0 Cu* 17.1 Ni* | — | 797.5 Au ([1,132.7 mg/L × 0.004 L]/ 0.125 g × 22 g) 37.1 Cu 1.8 Ni | 88.9% Au 28.1% Cu 10.5% Ni | Au:Cu 7:1 to 22:1 (3) Au:Ni 52:1 to 443:1 (9) |

*total metal mass contained in Pregnant lixiviant (250 mL).

Using the data in Table 10, the concentration factor from the biosorption process from 250 mL lixiviant and subsequent drying was calculated using the dry metal-laden biomass of 22 grams (Table 11).

TABLE 11

| Sample | Metal input concentration (mg/L [ppm]) | Metal output concentration (mg/kg [ppm]) | Increase in metal concentration (concentration factor) |
|---|---|---|---|
| *C. metallidurans* biosorption pellet | 3,589.3 Au 527.8 Cu 68.2 Ni | 36,250 Au (797.5 mg ÷ 0.022 kg) 1,686 Cu 82 Ni | 10.1 Au 3.2 Cu 1.2 Ni |

It can be seen that while gold increases in concentration by a factor of ~10, copper only increases in concentration by a factor of ~3, while nickel is found at similar levels.

Example 9: Recovery of Metal from Microorganism by Smelting

Materials and Methods:

Samples of metal laden microorganism (previously determined by atomic absorption spectrometry to contain 36,250 mg/kg [ppm] gold, 1,686 mg/kg copper, and 82 mg/kg nickel; see Example 8) were incinerated to remove organic matter and recover biosorbed metals.

1. 0.5 g of dried metal laden microorganism powder was mixed with equal portions of sodium tetraborate flux and placed in a crucible.
2. The mixture was carefully heated with a methylacetylene propadiene propane gas torch until the flux began to liquefy. The intensity of the flame was then gradually increased and the organic matter slowly burnt off.
3. The molten metal residue remaining in the crucible was coagulated into a single mass, allowed to cool, and subsequently weighed.
4. The cooled metal button was digested in 4 mL aqua regia, and the resultant solution analysed for total gold, copper and nickel content by atomic absorption spectrometry using a Shimadzu AA-6300 (Shimadzu Corp, Kyoto, Japan) as per the manufacturer's instructions.

Results:

The mass of the metal button achieved after smelting was 20.94 mg. Total metal content was reported as mg/L and used to calculate the metal yield (Table 10). Accuracy of total metal content was estimated at 15-20% variance.

TABLE 12

| Sample | Metal input (mg) | Metal content reported (mg/L [ppm]) | Metal recovered (mg) | Yield (% metal input) |
|---|---|---|---|---|
| Metal button from smelt | 18.12 Au (36,250 mg/kg × 0.0005 kg) 0.84 Cu 0.04 Ni | 5,493 Au 238 Cu 0 Ni | 21.97 Au (5,493 mg/L × 0.004 L) 0.95 Cu 0 Ni | 121% Au 113% Cu 0% Ni |

Example 10: Recovery of Gold from a Microorganism by Chemical Dissolution and Precipitation Materials and Methods:

Similarly to Example 9, biosorbed metal was recovered from the metal-laden microorganism by using a chlorine-based lixiviant extraction.

1. 100 mL of water was placed in a reaction vessel and charged with gaseous chlorine for 45 mins.
2. 0.3 g of dried metal-laden microorganism powder (see Example 8) was added to the lixiviant and allowed to react overnight while gently stirring.
3. The solution was then sparged with air to remove excess chlorine, and 0.5 g of sodium metabisulfite added to precipitate metal ions, such as gold, out of the solution.

Results:

The metal content of the metal laden microorganism powder was previously determined to be 36,250 ppm Au, 1,688 ppm Cu, and 82 ppm Ni (see Example 8). A visible precipitate formed in the solution after leaving for 24 hours at 22° C., which was gold powder.

General

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in the United States of America or any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A method of recovering a target metal from a pregnant aqueous solution containing the target metal, the method comprising:
   (a) providing a pregnant aqueous solution containing target metal ions;
   (b) a biosorption step comprising contacting a microorganism with the pregnant aqueous solution such that at least a portion of the target metal ions biosorb to the microorganism, wherein the microorganism becomes a metal laden microorganism and the pregnant aqueous solution becomes a barren solution;
   (c) separating the metal laden microorganism from the barren solution; and
   (d) recovering the target metal from the metal laden microorganism, wherein the pregnant aqueous solution includes at least one further metal, the microorganism preferentially biosorbs the target metal over the further metal in the biosorption step, and the further metal(s) remains in the barren solution in step (c).

2. The method of claim 1 wherein
   a) the pregnant aqueous solution contains more than 10 ppm of the target metal, or
   b) the barren aqueous solution contains less than 1 ppm of the target metal, or
   c) the concentration factor of the target metal from the pregnant aqueous solution to the microorganism is greater than 5.

3. The method of claim 1 wherein in the biosorption step the microorganism is in contact with the pregnant aqueous solution for between about 0.5 and 48 hours.

4. The method of claim 1 wherein the target metal is gold.

5. The method of claim 1 wherein the microorganism is a Gram-negative or a Gram-positive bacteria.

6. The method of claim 1 wherein the microorganism is selected from an environment where the target metal is found in a physiologically relevant amount.

7. The method of claim 1 wherein the separation step includes at least one of:
   gravity separation of the metal laden microorganism from the barren aqueous solution and removal of the barren solution;
   centrifugation and removal of the barren solution;
   filtration of the metal laden microorganism from the barren solution.

8. The method of claim 7 wherein at least 60% by volume of the barren aqueous solution is removed.

9. The method of claim 1 wherein the recovery step includes
   a) contacting the metal laden microorganism with a condition which triggers the microorganism to desorb the target metal, or
   b) burning or chemical dissolution of the metal laden microorganism to desorb the target metal.

10. The method of claim 9 wherein the condition that triggers desorption of the target metal is
    a) a solution containing a compound that triggers desorption of the target metal, wherein the compound is selected from the group consisting of cysteine, thiosulphate, thiourea, and any combination of two of more thereof; or
    b) a pH less than 5.

11. The method of claim 1 wherein the microorganism preferentially biosorbs the target metal over the further metal in the biosorption step such that the mass ratio of target metal to further metal in the microorganism increases by a factor of at least 2 when compared to the mass ratio in the pregnant aqueous solution.

12. The method of claim 1 wherein the further metal is selected from one or more of copper and nickel.

13. The method of claim 1, the method comprising:
    (a) providing the pregnant aqueous solution containing target metal ions in a dissolution step comprising dissolving the target metal from a solid feedstock material with a lixiviant to form the pregnant aqueous solution containing target metal ions.

14. The method of claim 13 wherein the solid feedstock material comprises a solid material comprising less than 5% of target metal.

15. The method of claim 13 wherein the solid feedstock material is any one or more of an ore, a tailing or e-waste.

16. The method of claim 13 wherein the target metal is gold, the solid feedstock material is e-waste, or gold bearing ore, or gold bearing sand, or gold bearing clay.

17. The method of claim 13 wherein the lixiviant is a thiourea-based solution, or a thiosulphate-based solution, or a thiocyanate-based solution, or a cyanide-based solution, or a halogen-based solution, or an aqua regia-based solution.

18. A target metal recovered by the method of claim 1.

19. The method of claim 1 wherein the pregnant aqueous solution containing target metal ions is formed by dissolving a target metal from a solid feedstock material with a lixiviant.

20. The method of claim 1 wherein the pregnant aqueous solution comprises a solution selected from the group consisting of a thiourea-based solution, a thiosulphate-based solution, a thiocyanate-based solution, a cyanide-based solution, a halogen-based solution, and an aqua regia-based solution.

* * * * *